United States Patent [19]

Zajac, Jr.

[11] Patent Number: 5,105,031
[45] Date of Patent: Apr. 14, 1992

[54] ENERGETIC MATERIAL

[75] Inventor: Walter W. Zajac, Jr., Newtown Square, Pa.

[73] Assignee: The United States of America as represented by the Secretary of the Army, Washington, D.C.

[21] Appl. No.: 718,318

[22] Filed: Jun. 17, 1991

[51] Int. Cl.$^5$ .................. C07C 79/08; C06B 25/00
[52] U.S. Cl. .................................. 568/941; 199/88
[58] Field of Search ...................... 149/88; 568/941

[56] References Cited

U.S. PATENT DOCUMENTS

| | | | |
|---|---|---|---|
| 3,006,971 | 10/1961 | Feuer et al. | 568/941 |
| 3,258,498 | 6/1966 | Schneider | 568/941 |
| 3,535,390 | 10/1970 | Driscoll | 568/941 |
| 4,329,522 | 5/1982 | Gilbert et al. | 568/941 |
| 4,535,193 | 8/1985 | Sollott et al. | 568/941 |

OTHER PUBLICATIONS

Leibzon et al., *Chem. Abs.*, 86, p. 567, Abs. #86:98011c, (1977).

*Primary Examiner*—Edward A. Miller
*Attorney, Agent, or Firm*—Anthony T. Lane; Edward Goldberg; Edward Costigan

[57] ABSTRACT 3,7,9-Trinitronoradamantane and a method of making the same.

1 Claim, No Drawings

ENERGETIC MATERIAL

GOVERNMENTAL INTEREST

The Government has rights in this invention pursuant to Contract No. DAAK10-85-C-0075 awarded by Department of the Army.

FIELD OF USE

This invention relates to an improved energetic material which may be used in the explosive art by the military.

BACKGROUND

It is well known that caged molecules are highly strained and energetic. It is also known that when nitro groups are added to a strained caged structure it is very explosive.

SUMMARY OF INVENTION

It is an object of this invention to provide a multi-nitrated caged molecule which is highly energetic.

Another object is to produce 3,7,9-Trinitronoradamantane.

A further object is to provide a process of making the cited compound.

PREFERRED EMBODIMENT

Specific Example

Into a 50 mL round-bottomed flask equipped with magnetic stirrer and reflux condenser was added (2.74 g, 0.0129 mol) 9,9-dimethoxybicyclo(3.3.1)nonan-3,7-dione prepared by the procedure of Stetter and Lennartz, Ann.de Chemie, 1977, 1807, redistilled pyridine (10 mL), and methanol (20 mL). Hydroxylamine hydrochloride (2.10 g, 0302 mol) was added and the mixture refluxed for 3 h.

The mixture was cooled to room temperature and added to a 125 mL separatory funnel which contained 25 mL ice water. This mixture was extracted with methylene chloride (4×25 mL). The combined extracts were washed with water (1×25 mL), dried with anhydrous sodium sulfate and concentrated under reduced pressure. Removal of trace solvent under high vacuum afforded a light yellow-white solid (2.04, 65%, m.p. 210°-213°(dec.). Anal.Calcd for $C_{11}H_{18}O_4N_2$: C,54.51; H,7.48; N,11.61. Found: C,54.50; H,7.43; N,11.32.

9,9-Dimethoxy-3,7-dinitronoradamantane

Into a 3-neck 1000 mL round-bottomed flask equipped with magnetic stirrer, reflux condenser, and source of nitrogen (Firestone valve) was added 9,9-dimethoxy-(3.3.1)bicyclonona-3,7-dione bis oxime (1.71 g, 7.066 mmol), finely ground urea (1.20 g, 20 mmol), anhydrous disodium hydrogen phosphate (7.2 g, 50.7 mmol), and sieve drive acetonitrile (200 mL). This mixture was heated to reflux for 10-15 min. 3-Chloroperbenzoic acid (12.7 g, 80-85%) was added in four increments over a 1 h period; reflux was then continued an additional 2½ h.

The cooled reaction mixture was freed of solvent in vacuo and the residue extracted with methylene chloride (3×100 mL). The combined extracts were washed with saturated sodium hydrogen carbonate solution (4×50 mL) and water (1×50 mL). The organic solution was dried with anhydrous sodium sulfate and the solvent was removed under reduced pressure to yield a crude solid.

The crude produce was redissolved in methylene chloride, washed with a solution of sodium hydrogen carbonate, then passed through a pad of silica gel. Separation by prep plate silicia gel chromatography of this residue gave (0.84 g, 75%) of the product.

3,7-Dinitro-9-noradamantanone

A stirred solution of 9,9-dimethoxy-3,7-dinitro-(3.3.1) bicylcononane (0.286 g, 1.05 mmol), methanol (3 mL), and 6N hydrochloric acid (40 mL) was refluxed for 18 h.

The mixture was cooled to room temperature and transferred to a 125 mL separatory funnel and extracted with methylene chloride (2×50 mL). The organic layer was dried with anhydrous sodium sulfate and concentrated under reduced pressure. Removal of trace solvent under high vacuum afforded the product as a white amorphous solid (0.2383 g, 71%). IR(cm$^{-1}$) 3000-2800 (w), 1736(m), 1549(s), 1360(m). 200 MHz $^1$H NMR(CDCl$_3$) δ2.55 (d,J=9.73, 4H), 3.05(m,6H). 50.3 MHz $^{13}$C NMR(CDCl$_3$) δ46.11(t), 48.07(d), 93.10(s), 205.19(s).

3,7-Dinitro-9-noradamantanone Oxime

Into a 10 mL round-bottomed flask equipped with a reflux condenser and magnetic stirrer was placed 3,7-dinitro-9-noradamantanone (0.170 gm, 0.75 mmol), redistilled pyridine (2.5 mL), and ethanol (3 mL, 95%). Hydroxylamine hydrochloride (0.20 gm, 2.88 mmol) was added and the mixture heated to a mild reflux (110°) for 1.25 h.

The mixture was cooled to room temperature with an ice bath and put in a 125 mL separatory funnel with methylene chloride (40 mL) and water (10 mL). The extracted organic layer was dried with anhydrous sodium sulfate and the solvent was removed in vacuo. The aqueous layer was extracted again with methylene chloride (40 mL), dried, and again removed in vacuo. Excess pyridine was removed under high vacuum to afford and off-white amorphous solid (0.1538 gm, 85%) m.p. 262-5(dec.) IR(cm$^{-1}$) 3350-3000(br), 3000-2800(br), 1559. 200 mHz, $^1$H NMR (acetone-d$_6$) δ32.63, 40.96, 46.88, 95.51, 155.45. Anal.Calcd for $C_9H_{11}O_5N_3$: C, 44.82; H, 4.60; N, 17.42. Found: C, 44.44; H, 4.45; N, 17.10.

9-Chloro-3,7,9-trinitronoradamantane

Into a 25 mL round-bottomed flask equipped with magnetic stirrer was added (97.6 mg, 0.405 mmol), ethylacetate (5 mL), and water (4 mL). After stirring 5 min, sodium hydrogen carbonate (0.44 gm, 5.24 mmol) was added followed by 1-sodio-3,5-dichloro-1,3,5-triazene-2,4,6(1H, 3H, 5H) trione (0.36 g, 20.45 mmol). The rapidly stirred mixture which turned blue-green with 90 sec. was stirred overnight.

After 20 h, the reaction mixture was placed in a 125 mL separatory funnel with ethylacetate (50 mL). The aqueous layer was drained off while the organic layer was washed with water (2×20 mL). After drying the organic layer with anhydrous sodium sulfate, the solvent was removed in vacuo to give a white amorphous solid (0.0849 g, 72%). 50.3 mHz, $^{13}$C NMR(CDCl$_3$) δ42.72, 44.25, 45.51, 91.12, 92.70, 100.38.

3,7-Dinitro-9-hydroxylaminonoradamantane

A 250 mL round-bottom flask fitted with a magnetic stirrer and nitrogen source (Firestone valve) was charged with 3,7-dinitro-9-noradamantanane oxime (1.14 gm, 4.73 mmol) and glacial acetic acid (50 mL). The mixture was cooled using an ice bath until the beginning of solidification. Then sodium cyanoborohydride (0.1 gm, 1.6 mmol) was added and the mixture was rapidly stirred under nitrogen while allowing it to come to room temperature. After 1 h sodium cyanoborohydride (0.1 gm, 1.6 mmol) was again added and stirring continued under nitrogen for an additional 3 h at room temperature.

The acetic acid was removed under reduced pressure and high vacuum to leave a crude residue (2.07 gm). The residue dissolved in 70 mL ethyl acetate and 30 mL water to which gm of sodium hydroxide pellets has been added. The alkaline solution was extracted again with ethyl acetate (4×50 mL), the fractions combined and washed with water (1×25 mL). The organic layer was dried with anhydrous sodium sulfate and evaporated in vacuo to give a hydroscopic slightly yellow solid (0.56 g, 49%). IR (Cm$^{-1}$) 15.49. 50.3 mHz, 13 NMR (acetone-d$_6$) §37.60, 42.95, 45.23, 61.47, 95.74, 96.10.

3,7,9-Trinitronoradamantane

A 100 mL round-bottomed flask containing 30–35 mL chloroform was cooled in a dry ice/acetone bath and saturated with ozone (blue color). With continual ozonation a solution of 3,7-dinitro-9-hydroxylaminonoradamantane (0.52 gm, 2.14 mmol) in chloroform (25 mL) and ethylacetate (5 mL) was added dropwise over a 15 min. period. Ozonation was continued another 10 min after which the solvent was removed under reduced pressure to afford a white amorphous solid. This is a 3,7,9-trinitronoradamantane having a mp>300°. (0.4861 gm, 88%) IR(KBr, cm$^{-1}$) 1541. 50.3 mHz, $^{13}$C NMR (CDCl$_3$) §38.60, 43.69, 44.42, 83.02, 93.00, 93.54. Anal.calcd for $C_9H_{11}N_3O_6$: C, 42.03; H, 4.31; N, 16.34. Found: C, 41.87; H, 4.09; N, 16.09.

What is claimed is:
1. 3,7,9-Trinitronoradamantane.

* * * * *